United States Patent [19]

Farkas et al.

[11] Patent Number: 5,710,069
[45] Date of Patent: Jan. 20, 1998

[54] MEASURING SLURRY PARTICLE SIZE DURING SUBSTRATE POLISHING

[75] Inventors: Janos Farkas; James Michael Mullins, both of Austin, Tex.

[73] Assignee: Motorola, Inc., Schaumburg, Ill.

[21] Appl. No.: 703,322

[22] Filed: Aug. 26, 1996

[51] Int. Cl.$^6$ ................................................ G01N 15/14
[52] U.S. Cl. ............................ 438/7; 438/8; 438/16; 438/747; 216/85; 451/6; 156/345 LC
[58] Field of Search ............... 216/85, 88; 156/626.1, 156/636.1, 345 LC; 437/7, 8; 356/336; 451/1, 6

[56] References Cited

U.S. PATENT DOCUMENTS

| | | | |
|---|---|---|---|
| 4,180,735 | 12/1979 | Sipila et al. | 250/358 R |
| 4,890,920 | 1/1990 | Niziolek et al. | 356/336 |
| 4,910,155 | 3/1990 | Cote et al. | 437/8 |
| 5,063,301 | 11/1991 | Turkevich et al. | 356/336 |
| 5,619,043 | 4/1997 | Preikschat et al. | 356/336 |

OTHER PUBLICATIONS

Pohl et al "semiconductor Process Measurement" Readout, No. 13, abstract only, 1996.

Adams et al "CMP slurry particle size spectrometer" IEEE/UCS/SEMI Intl. Symp on Semicond. Manuf., abstract only, 1995.

Julius Z. Knapp, "A Systems Analysis of Light Extinction Particle Detection Systems", R&D Associates Inc., Somerset, NJ, pp. 283–352.

P.J. Freud et al., "A New Approach to Particle Sizing by Dynamic Light Scattering", pub.by Leeds+Northrup to 1990 Pittsburgh Conf. in New York, Mar. 5–9, 1990, pp. 1–8.

P.J. Freud et al., "Unified Scatter Technique for Full–Range Particle Size Measurement", pub. by Leeds+Northrup to Pittsburgh Conf., Mar. 8–12, 1993, pp. 1–7.

"How to characterize submicron particles . . . without dilution" pub. by Leeds+Northrup/1994, pp. 1–2.

"The AccuSizer™ 770 Optical Particle Sizer", pub. by Particle Sizing Sys., pp. 1–2.

"Particle Analysis in Concentrated Suspensions", pub. by Brookhaven Instruments Corp., pp. 1–2.

Julius Z. Knapp, Carleton's Corner: "Particulate Matter Counting: The Technical Issues", pub. by Journal of Parenteral Science and Tech., vol. 42, No. 1/Jan.–Feb. 1988, pp. 1–8.

Dr. Robert G. Knollenberg et al., "Refractive Index Effects on Particle Size Measurement . . . ", pub. by pp. 154–182.

Alvin Lieberman, "Problems Associated With Submicrometre Contaminant Measurement", pub. by ASTM Special Tech. Pub. 850, for Semiconductor Equip./Mat. Inst. Feb. 7–10, 1984, pp. 172–183.

D. F. Nicoli et al., "Automatic, high-resolution particle size analysis", pub. by American Lab., Jul. 1992, pp. 39–44.

D.F. Nicoli et al, "Wide dynamic range particle size analysis by DLS–SPOS", pub. by American Lab., Apr. 1995, pp. 41–49.

R. Nagahara et al., "The Effect of Slurry Particle Size on Defect Levels for a BPSG CMP Process", pub. by Particle Sizing Sys., Jun. 18–20, 1996 VMIC Conf., p. 1.

Primary Examiner—R. Bruce Breneman
Assistant Examiner—Anita Alanko
Attorney, Agent, or Firm—George R. Meyer

[57] ABSTRACT

A method of sensing a particle in a mixture includes providing (52) the mixture (36) having a particle (29, 30), moving (54) the mixture (36) in a direction, shining (56) a light into a portion of the moving mixture (36), reflecting a portion of the light off of the particle (29, 30) in the moving mixture (36), detecting and measuring (57) the reflected light, and using (58) the measured reflected light to determine a size of the particle (29, 30).

22 Claims, 3 Drawing Sheets

MEASURING SLURRY PARTICLE SIZE DURING SUBSTRATE POLISHING

FIELD OF THE INVENTION

This invention relates, in general, to process for forming semiconductor devices, and more particularly, process for forming semiconductor devices using chemical-mechanical polishing.

BACKGROUND OF THE INVENTION

Processes for manufacturing semiconductor devices often include a chemical-mechanical polishing (CMP) step to improve the planarity of a dielectric or metal layer. The CMP step uses a slurry containing small abrasive particles that are typically less than about one micron in diameter. However, when the slurry contains large particles having diameters on the order of several tens of microns, the CMP process does not produce a uniform and planar surface. Instead, the polished surface contains many pits, residues, and other surface anomalies. Therefore, the size of the abrasive particles in the slurry should be monitored and controlled.

One off-line monitoring technique uses a light blockage concept wherein a beam of light is shined into a small sample of the slurry, which is heavily diluted. The amplitude of a negative light pulse, which is the blocked light, is proportional to the size of the particle passing through the beam of light. For reasons understood by those skilled in the art, the slurry must be heavily diluted for this monitoring technique to work properly because only one particle should pass through the beam of light at a time. However, the colloidal properties of the slurry are altered as a result of the dilution. Furthermore, by heavily diluting the slurry, additional particles can be added to the slurry by the diluent. As a result, the dilution will distort the measured particle size distribution of the slurry. Additionally, this light blockage technique is a troublesome in-line process because a small sample of the slurry must first be extracted and then diluted before being analyzed. Consequently, the analysis is done off-line and a significant delay can exist between the extraction of the slurry sample and the determination of the monitoring results. Thus, this light blockage technique does not provide timely or real-time feedback.

A second monitoring technique, known in the art as photoncorrelation spectroscopy or an "ensemble" method, shines a light into a diluted slurry that is stationary and then detects a portion of the light that is reflected off of a particle in the slurry. The measured portion of light or the measured signal is a fluctuating intensity around an average value. Changes in the intensity of the reflected light are due to the thermal or Brownian motion of the particles, and the changes in light intensity are used to mathematically estimate an average particle size, which can be calculated in the frequency domain or in the time domain. Therefore, photoncorrelation spectroscopy is not suitable for in-line measurements because the slurry must be stationary during the measurement.

Photoncorrelation spectroscopy estimates the mean particle size in the slurry and does not provide accurate information concerning a tail portion of the particle size distribution. Without knowing the tail of the distribution, large particles in the slurry will not be detected by this second monitoring technique, and the large particles will produce defects in the substrate being polished. Even the presence of a single large particle in the slurry can scratch the substrate and produce other defects in the polished surface. Furthermore, photoncorrelation spectroscopy can also produce highly inaccurate results if the particles have a bimodal distribution wherein the ratio of the population between the two modes is 3:1 or greater.

Accordingly, a need exists for a method of sensing particles in a mixture wherein, the method is suitable for in-line or off-line monitoring, wherein the mixture does not need to be diluted, and wherein a tail of the distribution of particle size can be accurately measured.

DETAILED DESCRIPTION OF THE DRAWINGS

Figure 1:
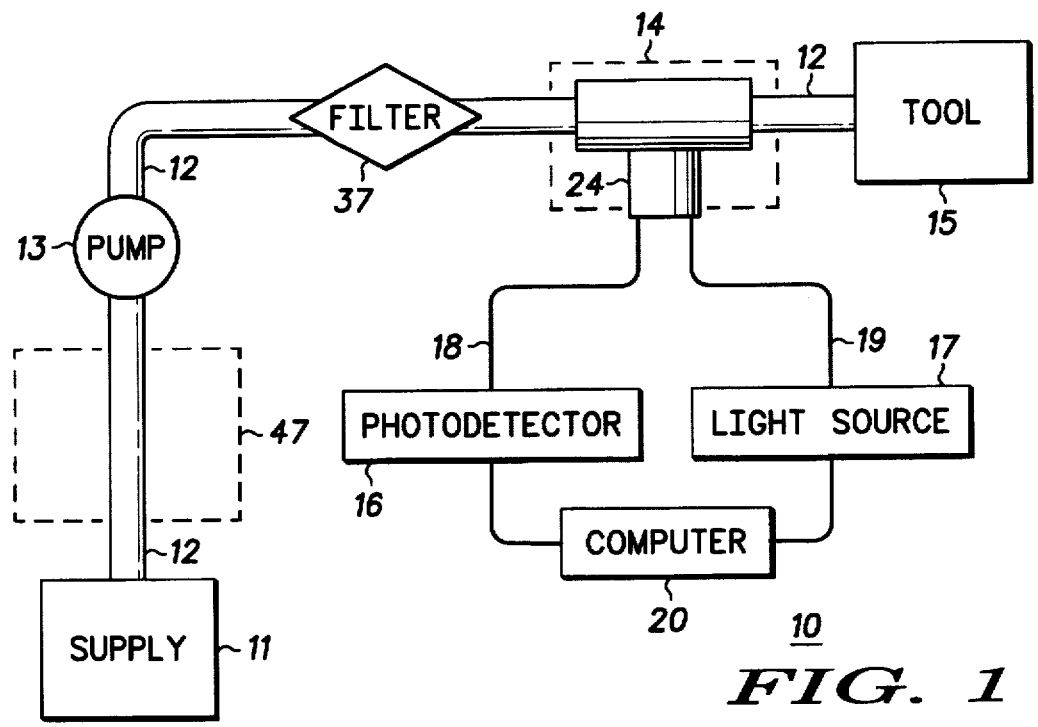
FIG. 1 illustrates a schematic view of a system for sensing a particle in a mixture in accordance with the present invention.

FIG. 1 illustrates a schematic view of a system 10 for sensing a particle in a mixture. System 10 includes a supply 11 of the mixture and a processing tool 15 that contains a workpiece (not shown) to be processed by the mixture. It is understood that the mixture is a liquid that includes particles (i.e., a slurry), and it is further understood that the workpiece is any object to be processed by the mixture. As an example, the mixture can be a slurry used for a chemical-mechanical polishing (CMP) process; the workpiece can be a semiconductor device substrate comprised of dielectric and metals layers overlying a semiconductor layer; and tool 15 can be a semiconductor processing tool, such as a CMP tool, as known in the art. Typically, a CMP slurry is an optically transmissive mixture that includes a fluid and a plurality of abrasive particles that have a different refractive index than that of the fluid wherein the abrasive particles are of different sizes below approximately one micron in diameter.

If desired, the mixture can be passed through an optional filter 37 to purify the mixture prior to analyzing the mixture and prior to using the mixture in tool 15. The mixture can be passed through an analytical section 14 of system 10 to measure the effectiveness of filter 37 and to ensure the quality of the mixture prior to using the mixture in tool 15. When the mixture enters the analytical section 14, the mixture usually has a particle concentration in a range of approximately 1–25 weight percent, and more typically in a range of approximately 2–12 weight percent. The mixture preferably passes through section 14 at a substantially constant rate or speed for reasons explained hereinafter. As an example, a pump 13 can be used to displace, conduct, move, or pump the mixture in a substantially constant motion or speed from supply 11, through filter 37, through section 14, and towards the workpiece in tool 15. The mixture is guided through a coupling line 12 to the different portions of system 10. Line 12 couples supply 11, pump 13, filter 37, section 14, and tool 15. As an example, pump 13 can be a peristaltic pump, and coupling line 12 can be flexible tubing having a diameter of less than approximately two centimeters. The flexible tubing can be Teflon™ tubing, which is manufactured the E. I DuPont de Nemours and Company of Wilmington, Del.

A light source 17 and a photodetector 16 are coupled to analytical section 14 through optical lines 19 and 18, respectively. A computer 20 is coupled to light source 17 and photodetector 16 to control light source 17, to interpret data from photodetector 16, and to accurately calculate a tail of the overall distribution of particles in the mixture. Light source 17 generates a light beam, and section 14 shines the light beam into coupling line 12. Photodetector 16 senses or detects light reflected from the particles in a portion of the mixture that passes through section 14. It is understood that a plurality of light sources and a plurality of photodetectors can be used in system 10. It is also understood that an analytical section 47, which is similar to section 14, can be used in place of or in addition to section 14. When section 47 is used in place of section 14, section 47 can be coupled to photodetector 16 and light source 17 in a similar manner to that shown for section 14. As examples, light source 17 can be a gallium arsenide red laser diode; photodetector 16 can be a photomultiplier or a photodiode; and computer 20 can include a frequency-voltage converter for photodetector 16 when photodetector 16 is a photomultiplier, an amplifier to increase the electrical signal from photodetector 16, an analog-to-digital converter to translate the signal from photodetector 16, a timing and counting circuit, or the like. In addition to light, other radiation sources could be used, such as infrared, ultraviolet, etc. The radiation needs to be transparent to the liquid medium.

Figure 2:
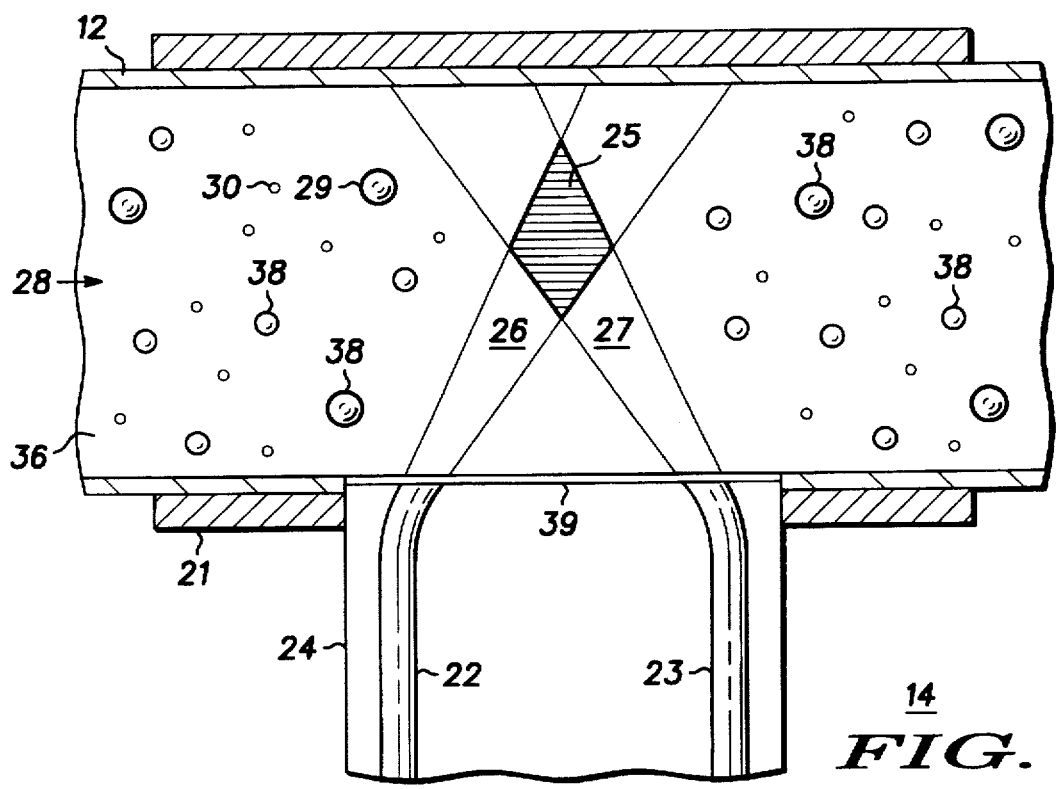
FIG. 2 portrays a cross-sectional view of a section of the system of FIG. 1 in accordance with the present invention.

FIG. 2 portrays a cross-sectional view of section 14 in system 10. It is understood that the same reference numerals are used in the figures to denote the same elements. FIG. 2 illustrates a mixture 36 having a plurality of particles 29, 30, and 38 passing through coupling line 12 in section 14 of system 10. An optical alignment line 23 is coupled to line 19 (FIG. 1) and carries or conducts an incident light beam generated by light source 17 (FIG. 1) into coupling line 12. The incident light beam has a light cross-section 27 within coupling line 12. Another optical alignment line 22 is coupled to line 18 (FIG. 1) and carries or conducts light reflected from plurality of particles 29, 30, and 38 to photodetector 16. Alignment line 22 generates a detection cross-section 26 within coupling line 12.

Alignment lines 22 and 23 are positioned within a housing 24 that is attached to coupling line 12 with a clamping device 21. As examples, optical lines 18 and 19 (FIG. 1) and alignment lines 22 and 23 can be optical fibers, as known in the art. Alignment lines 22 and 23 are positioned such that cross-sections 26 and 27 intersect to form a sampling or scattering volume 25 within coupling line 12. As mixture 36 moves in a direction indicated by an arrow 28 through coupling line 12, a particle 29 will pass through scattering volume 25 and will be detected by system 10. Subsequently, a particle 30, which is smaller than particle 29, will also pass through scattering volume 25 and will also be detected by system 10, as explained hereinafter.

Detection cross-section 26, light cross-section 27, and the wavelength of the incident light beam should not be significantly distorted when passing through the wall of coupling line 12. If necessary, a portion of the wall of coupling line 12 can be replaced with a different material 39 that does not significantly distort cross-sections 26 and 27 or the wavelength of the incident light beam. As an example, a piece of glass, quartz, or high quality plastic can be used for material 39.

Figure 3:
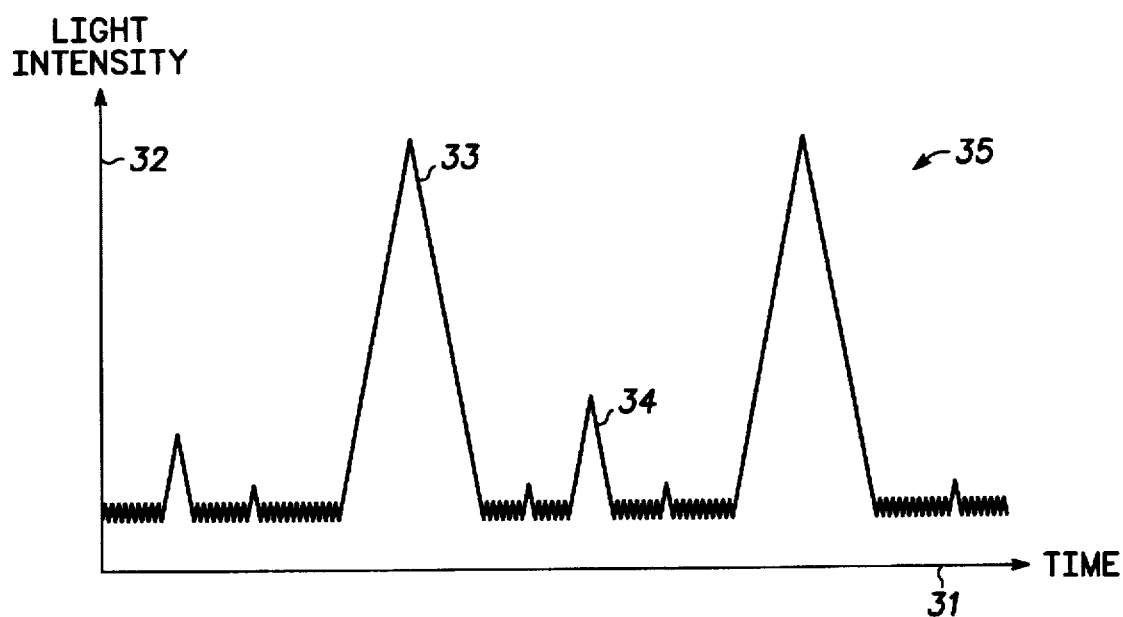
FIGS. 3 and 4 are graphs illustrating data measured by the system in accordance with the present invention.
Figure 4:
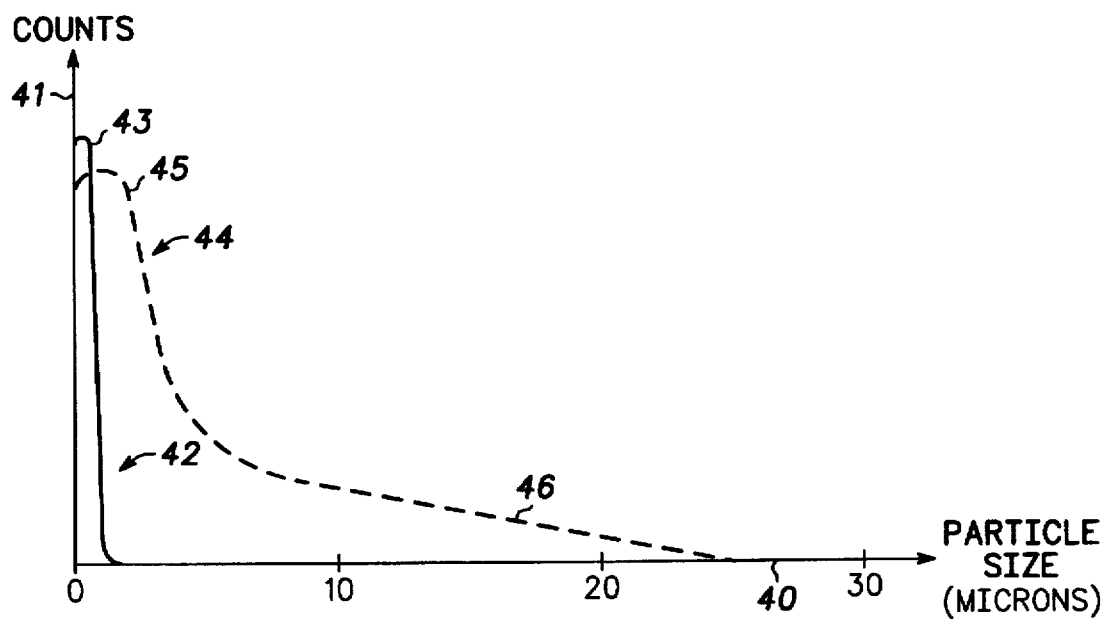

FIGS. 3 and 4 are graphs illustrating data measured by system 10. FIG. 3 depicts a spectrum 35 plotted on a graph having an x-axis 31 that represents time and a y-axis 32 that represents an intensity of light measured by photodetector 16 (FIG. 1). Each peak in spectrum 35 represents a different particle in mixture 36 (FIG. 2) that passes through volume 25 (FIG. 2) wherein the detected intensity of reflected light in FIG. 3 is highly nonlinear to the size of the particle that passes through volume 25. As known in the art, it is common practice to identify the reflected light as a scattered light when the size of the measured particle is similar to or smaller than a wavelength of the light. However, to facilitate the explanation of the present invention, the term "reflected light" is used interchangeably with the term "scattered light."

The intensity of reflected or scattered light may be exponentially proportional to the particle size. Therefore, an intensity of light peak 33, which is higher or greater than an intensity of light peak 34, represents a larger particle in mixture 36 compared to peak 34. Accordingly, a large particle is much easier to detect compared to a small particle because the light intensity increases non-linearly. As an example, peak 33 can represent particle 29 (FIG. 2) passing through volume 25 and reflecting or scattering light from the incident light beam into detection cross-section 26. Similarly, peak 34 can represent the subsequent detection of particle 30 (FIG. 2) passing through volume 25 and reflecting or scattering light from the incident light beam into detection cross-section 26. Peak 33 is higher than peak 34 because particle 29 is larger than particle 30 and reflects more light than particle 30.

To ensure that each peak of spectrum 35 represents a single particle in mixture 36, volume 25 should be small enough to ensure that no more than one particle is detected by the photodetector 16 at any point in time. Alignment lines 22 and 23 can be adjusted accordingly. Still, more than one particle at a time may lie within the volume 25, as long as, all other particles are not detected by the photodetector 16. If photodetector 16 detects two or more particles at once, then spectrum 35 would incorrectly indicate the presence of a large particle by showing a large single peak when, in fact, two separate smaller peaks should be measured.

As the particle concentration within the mixture increases, the scattering volume 25 is typically decreased. Furthermore, if volume 25 were too large, the measurement results of system 10 may suffer from secondary optical scattering where light is reflected off of more than one particle prior to being detected. Thus, secondary scattering incorrectly increases the intensity of the reflected light from a particle and should be avoided. The scattering volume 25 should be at least as large as the normally anticipated largest particle size. The scattering volume 25 may also be affected by the concentration of the particles. The scattering volume 25 is a function of the shape of the detector sensor. For example, if the mixture 36 includes a particle concentration in a range of 1–10 weight percent, one type of detector sensor is used. If the particle concentration in the mixture 36 is in a range of 11–20 weight percent, a different detector sensor is used that creates a smaller scattering volume 25.

Furthermore, the flow rate of mixture 36 through section 14 should be substantially constant while measuring the size of the particles in mixture 36 in order to ensure that the widths of the individual peaks of spectrum 35 are substantially proportional to the length of time that the particles are in detected by the photodetector 16 (FIG. 2). The actual preferred flow rate is dependent upon various factors including the size of the particles to be measured, the concentration of the particles, and the size of volume 25.

Computer 20 (FIG. 1) uses spectrum 35 to create a distribution of the size of the particles in mixture 36. FIG. 4 depicts a graph of two distributions wherein an x-axis 40 represents particle size and wherein a y-axis 41 represents a count or number of particles. A distribution 42, shown by a solid line, represents a preferred distribution for a CMP slurry because distribution 42 has a count peak 43 of particles having diameters less than approximately one micron. Distribution 42 does not include significant numbers of large particles.

However, a distribution 44, shown by a dashed line in FIG. 4, has a count peak 45 that is undesirable for a CMP slurry because a tail portion 46 of peak 45 indicates the presence of particles having a size greater than a predetermined threshold or maximum size of, for example, approximately one micron. As an example, count peak 45 can represent the presence of a plurality of particles that each reflect an intensity of light similar to intensity of light peak 34 (FIG. 3), and tail portion 46 can represent the presence of a plurality of particles that each reflect an intensity of light similar to intensity of light peak 33 (FIG. 3). A mathematical translation of the data from spectrum 35 of FIG. 3 to distribution 44 of FIG. 4 is known to those skilled in the art. For example, calibration curves can be used in the mathematical translation. The present method of particle size monitoring provides accurate information concerning tail portion 46 because the intensity of reflected light is non-linearly proportional to particle size. Therefore, larger particles are much easier to detect compared to smaller particles.

The system 10 including the analytical section 14 can be used to detect particle distributions in mixtures having a particle concentration in a range of approximately 1–25 weight percent. Prior art techniques may only be able to determine particle information in a flowing liquid stream only if the particle is significantly less than one weight percent. The particular combination of components of embodiments of the present invention allows particle information to be collected in a liquid stream having a particle concentration similar to many slurries used in CMP processes.

The prior art technique of photoncorrelation spectroscopy will not be able to determine distribution 44 because photoncorrelation spectroscopy estimates the mean particle size and does not provide accurate information concerning the tail or tails of the particle size distribution. Photoncorrelation spectroscopy only estimates the mean of a particle distribution based upon a measurement of reflected light from a stationary mixture wherein the changes in reflected light intensity from one instant in time to another are used to estimate an mean particle size. Therefore, photoncorrelation spectroscopy will determine that a slurry having a particulate distribution similar to distribution 44 is acceptable for polishing a substrate when, in fact, it is not acceptable. As discussed earlier, even a single large particle in a CMP slurry can produce a non-uniformly polished surface that includes many defects. Furthermore, because the mixture is stationary and because photoncorrelation spectroscopy relies upon Brownian or thermal motion of the particles, the same particle may be measured over and over again in the prior art technique. However, the same particle will not be measured more than once by the present method because the mixture being measured is moving or flowing in a particular direction.

Figure 5:
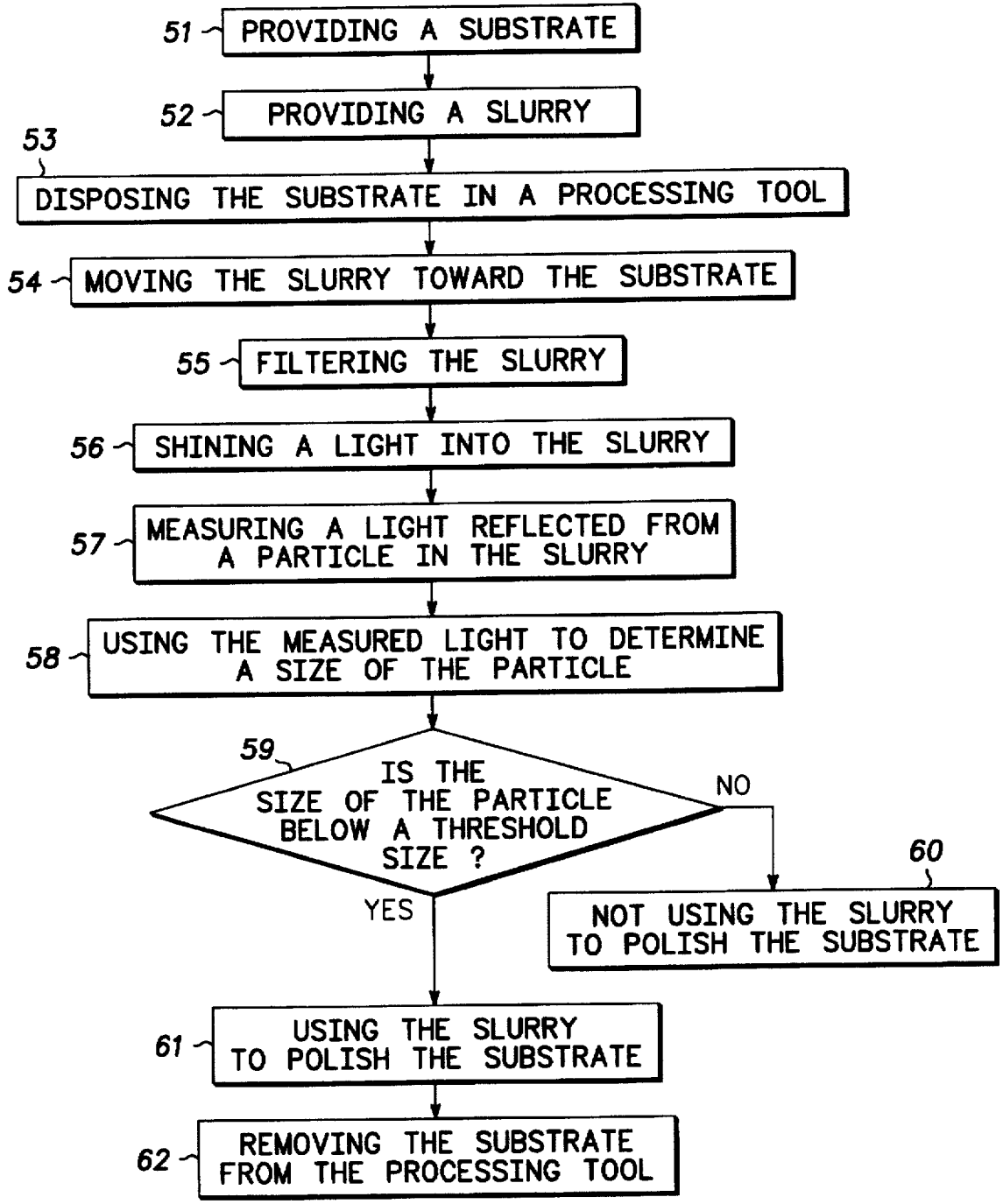
FIG. 5 outlines a method of monitoring a particle in a mixture in accordance with the present invention.

FIG. 5 outlines a method 50 of detecting, sensing, or monitoring a particle in a mixture, as described hereinbefore with reference to FIGS. 1, 2, 3, and 4. The particle monitoring steps of method 50 are described in relationship to manufacturing or fabricating a semiconductor device or component. A step 51 of method 50 provides a workpiece or substrate, and a step 52 provides a mixture or slurry having a plurality of particles. The substrate is disposed in a processing tool during a step 53, and the slurry and its plurality of particles are moved, guided, or pumped toward the substrate in a step 54. Afterwards, an optional step 55 filters a portion of the slurry prior to steps 56, 57, and 58, which analyze or measure the size of the particles in the portion of the mixture. Step 55 also occurs prior to a step 59, which uses the portion of the mixture to process the substrate. However, if section 47 (FIG. 1) is used in place of section 14 (FIG. 1), then step 55 can alternatively be performed after steps 56, 57, and 58.

Step 56 shines an incident light into the filtered portion of the slurry. Different portions of the incident light or different intensities of light are reflected off of the various sizes of particles in the portion of the slurry. Then, step 57 monitors, detects, or measures the reflected light off of the particles in the portion of the slurry. Steps 56 and 57 are sequentially repeated to measure different particles in the slurry. The reflected light from a first particle should be detected prior to reflecting or detecting additional light from a second particle for reasons discussed hereinbefore. During steps 56 and 57, the plurality of particles in the portion of the slurry are preferably moving in a substantially constant motion or at a substantially constant rate or speed wherein the vector sum of the velocity of all of the particles in the portion of the slurry is greater or less than zero. In the prior art technique of photoncorrelation spectroscopy, the vector sum of the velocity of all the particles in the slurry is approximately equal to zero because of the Brownian or thermal motion of the particles.

Next, the reflected light that was detected or measured in step 57 is used to determine a size of the particle during step 58, and as steps 56 and 57 are repeated, step 58 determines a tail portion of a size distribution of the plurality of particles in the slurry. Then, a decision is made in a step 59 to determine a flow path for the mixture after leaving the particle analyzer. If the tail portion of the distribution of particle size exceeds or is not below a threshold or predetermined maximum size, then the slurry is prevented from contacting the substrate and is not used to polish the substrate, as indicated in a step 60. As an example, pump 13 (FIG. 1) can be stopped, and the slurry can be diverted away from tool 15, or coupling line 12 can be disconnected from tool 15 to flush the slurry out of line 12.

However, if the tail portion of the distribution of particle size is below a threshold size, then the measured slurry is applied to the substrate in the processing tool to chemically and mechanically polish the substrate as noted in step 61. Afterwards, the substrate is removed from the processing tool during a step 62. The particle concentration in the slurry is preferably kept at a substantially constant level between and during steps 56, 57, 58, and 59. In the prior art, the diluent can change the particle size distribution by changing the colloidal properties of the slurry or by adding additional particles to the slurry.

Therefore, it is apparent there has been provided an improved method of sensing a particle in a mixture that overcomes the disadvantages of the prior art. The method described herein provides single-particle detection in a concentrated or undiluted suspension or mixture and provides an accurate determination of the tail portion of the distribution of the particles in the mixture. The present method does not require mixture dilution so that the colloidal properties of the mixture are not altered during the measurement of particle size. The method is also less susceptible to contamination because the mixture is not diluted. Furthermore, the method provides in-line and real-time data for monitoring particles within a moving or flowing mixture.

While the invention has been particularly shown and described with reference to preferred embodiments, it will be understood by those skilled in the art that changes in form and detail may be made without departing from the spirit and scope of the invention. Other embodiments are not limited to CMP processes. For example, any process that requires monitoring particles in a liquid stream, such as semiconductor wafer polishing, back lapping finished substrates, and the like, can take advantage of the benefits that accrue by using an embodiment of the present invention.

The particle detection method can be used before and after a filtering step to test or check the effectiveness of the filtering step. Additionally, the filtering step can occur after the mixture is used to process a workpiece so that the mixture is recycled or recirculated in order to reduce manufacturing costs. Furthermore, the filtering method can be used to determine when an automatic line flush is necessary to clean coupling line 12 (FIG. 1) when the particulate size exceeds a predetermined limit. Moreover, when section 47 (FIG. 1) is used in place of section 14 (FIG. 1), then the monitoring method can be used to determine the quality of the slurry as it is immediately extracted from supply 11 (FIG. 1). A light source and a photosensor can be positioned within coupling line 12 (FIG. 2) to directly contact mixture 36 (FIG. 2) if the light source and the photosensor are not chemically or physically etched or damaged by mixture 36. Although the method of particle detection is described in relationship to semiconductor applications, it is understood that the particle detection method can also be applied to pharmaceutical, petroleum, or other applications. Accordingly, the disclosure of the present invention is not intended to be limiting. Instead, the disclosure of the present invention is intended to be illustrative of the scope of the invention, which is set forth in the following claims.

We claim:

1. A process for forming a semiconductor device comprising steps of:
    providing a semiconductor device substrate within a tool;
    setting a particle size limit;
    flowing a liquid including particles through a particle analyzer having a detector, wherein only one particle at a time is detected by the detector; and
    determining a flow path for the liquid after leaving the particle analyzer, wherein the liquid:
        contacts the semiconductor device substrate within the tool if the only one particle is no larger than the particle size limit; and
        is diverted and does not contact the semiconductor device substrate within the tool if the only one particle is larger than the particle size limit.

2. The process of claim 1, wherein the step of providing is performed such that the tool is a chemical-mechanical polisher.

3. The process of claim 1, wherein the sampling volume is an intersection of a radiation beam and a detection cross section.

4. The process of claim 1, wherein the step of determining is performed such that all of the liquid that contacts the semiconductor device substrate flows through the particle analyzer at a substantially constant speed.

5. The process of claim 1, wherein the step of flowing is performed such that the particle size limit is one micron.

6. The process of claim 1, wherein the step of flowing is performed such that the liquid has a particle concentration of at least one weight percent.

7. The process of claim 1, wherein the step of flowing is performed such that the liquid has a particle concentration in a range of approximately 2-12 weight percent.

8. The process of claim 1, wherein the step of flowing is performed such that the liquid includes a plurality of different particle sizes.

9. The process of claim 1, further comprising a step of filtering the fluid before the step of flowing.

10. A process for forming a semiconductor device comprising steps of:
    providing a semiconductor device substrate within a chemical-mechanical polisher;
    flowing a slurry including particles through a particle analyzer having a detector, wherein only one particle at a time is detected by the detector;
    contacting the slurry with the semiconductor device substrate if the only one particle is no larger than a particle size limit after leaving the particle analyzer; and
    polishing the semiconductor device substrate after the step of contacting.

11. The process of claim 10, wherein the sampling volume is an intersection of a radiation beam and a detection cross section.

12. The process of claim 10, wherein the step of contacting is performed such that all of the slurry that contacts the semiconductor device substrate flows through the particle analyzer at a substantially constant speed.

13. The process of claim 10, wherein the step of contacting is performed such that the particle size limit is one micron.

14. The process of claim 10, wherein the step of flowing is performed such that the slurry has a particle concentration of at least one weight percent.

15. The process of claim 10, wherein the step of flowing is performed such that the slurry includes a plurality of different particle sizes.

16. The process of claim 10, further comprising a step of filtering the fluid before the step of flowing.

17. A process for forming a semiconductor device comprising steps of:
    providing a semiconductor device substrate within a chemical-mechanical polisher;
    flowing a slurry including particles including a first particle and a second particle through a particle analyzer having a detector, wherein only one particle at a time is detected by the detector, and wherein the first particle is smaller than the second particle;
    contacting the slurry with the semiconductor device substrate after the first particle flows through the particle analyzer but before the second particle flows through the particle analyzer;
    polishing the semiconductor device substrate after the step of contacting;
    detecting the second particle within the particle analyzer after the step of polishing commences; and
    terminating a flow of slurry to the semiconductor device substrate after the step of detecting.

18. The process of claim 17, wherein the sampling volume is an intersection of a radiation beam and a detection cross section.

19. The process of claim 17, wherein all of the slurry that contacts the semiconductor device substrate flows through the particle analyzer at a substantially constant speed.

20. The process of claim 17, wherein the step of flowing is performed such that the slurry has a particle concentration of at least one weight percent.

21. The process of claim 17, wherein the step of flowing is performed such that the slurry includes a plurality of different particle sizes.

22. The process of claim 17, further comprising a step of filtering the slurry before the step of flowing.

* * * * *